(12) United States Patent
Ehteshami et al.

(10) Patent No.: US 12,343,047 B2
(45) Date of Patent: *Jul. 1, 2025

(54) ANGLED SPINAL FIXATION PLATE

(71) Applicant: Additive Implants, Inc., Phoenix, AZ (US)

(72) Inventors: John R. Ehteshami, Paradise Valley, AZ (US); Mahyar Zoghi, Phoenix, AZ (US)

(73) Assignee: Additive Implants, Inc., Phoenix, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/433,230

(22) Filed: Feb. 5, 2024

(65) Prior Publication Data

US 2024/0350178 A1    Oct. 24, 2024

Related U.S. Application Data

(63) Continuation of application No. 17/400,735, filed on Aug. 12, 2021, now Pat. No. 11,903,618.

(51) Int. Cl.
  *A61B 17/70* (2006.01)
  *A61B 17/80* (2006.01)
  *A61F 2/44* (2006.01)

(52) U.S. Cl.
  CPC ...... *A61B 17/7059* (2013.01); *A61B 17/8042* (2013.01); *A61F 2/4455* (2013.01)

(58) Field of Classification Search
  CPC ............. A61B 17/7059; A61B 17/8042; A61F 2/4455; A61F 2/44; A61F 2/4461

USPC ...................... 606/70–71, 280–299, 300–321
  See application file for complete search history.

(56) References Cited

U.S. PATENT DOCUMENTS

| 5,261,910 | A | 11/1993 | Warden et al. |
|---|---|---|---|
| 5,324,290 | A | 6/1994 | Zdeblick |
| 5,549,612 | A | 8/1996 | Yapp et al. |
| 5,601,553 | A | 2/1997 | Trebing et al. |
| 7,306,605 | B2 * | 12/2007 | Ross .................. A61B 17/8042 606/70 |
| 8,556,944 | B2 * | 10/2013 | Dube ..................... A61B 90/94 606/295 |
| 8,845,697 | B2 * | 9/2014 | Montello ........... A61B 17/8057 606/280 |
| 2005/0192577 | A1 | 9/2005 | Mosca et al. |
| 2006/0036250 | A1 * | 2/2006 | Lange ................ A61B 17/8875 606/252 |
| 2006/0122602 | A1 | 6/2006 | Koxieczynski |

(Continued)

FOREIGN PATENT DOCUMENTS

| WO | 1992011819 | 7/1992 |
|---|---|---|
| WO | 1994006360 | 3/1994 |

(Continued)

OTHER PUBLICATIONS

Non-Final Office Action dated Oct. 13, 2022 in U.S. Appl. No. 17/400,735.

(Continued)

*Primary Examiner* — Jessica Weiss
(74) *Attorney, Agent, or Firm* — Snell & Wilmer L.L.P.

(57) ABSTRACT

The present invention relates to an implantable anterior cervical plate having a stackable superior design, which deflects soft tissue.

20 Claims, 7 Drawing Sheets

(56) References Cited

U.S. PATENT DOCUMENTS

| | | | | |
|---|---|---|---|---|
| 2009/0036933 A1* | 2/2009 | Dube | ............ | A61B 17/8615 |
| | | | | 606/301 |
| 2009/0062862 A1 | 3/2009 | Perrow et al. | | |
| 2009/0264934 A1 | 10/2009 | Youssef et al. | | |
| 2013/0090688 A1* | 4/2013 | Montello | ......... | A61B 17/7049 |
| | | | | 606/246 |
| 2013/0296938 A1* | 11/2013 | Birch | ............ | A61B 17/8047 |
| | | | | 606/246 |
| 2013/0345813 A1 | 12/2013 | Frank et al. | | |

FOREIGN PATENT DOCUMENTS

| | | |
|---|---|---|
| WO | 1995025474 | 9/1995 |
| WO | 1998051226 | 11/1998 |

OTHER PUBLICATIONS

Final Office Action dated Jun. 13, 2023 in U.S. Appl. No. 17/400,735.
Notice of Allowance dated Oct. 16, 2024 in U.S. Appl. No. 17/400,735.

* cited by examiner

ANGLED SPINAL FIXATION PLATE

CROSS-REFERENCE TO RELATED APPLICATIONS

This application is a continuation of, claims priority to and the benefit of, U.S. patent application Ser. No. 17/400,735 filed on Aug. 12, 2021 entitled "ANGLED SPINAL FIXATION PLATE". The contents of the above-identified application are herein incorporated by reference in its entirety.

FIELD OF THE INVENTION

The invention relates to spinal implants, and more particularly anterior angled spinal fixation plates having a superior tapered, angled, curved, or cambered shape.

BACKGROUND OF THE INVENTION

The human spinal column has more than twenty discrete bones sequentially coupled to one another by a tri joint complex that consists of an anterior disc and two posterior facet joints, the anterior discs of adjacent bones being cushioned by cartilage spacers referred to as intervertebral discs. The more than twenty bones are anatomically categorized in one of four classifications: cervical, thoracic, lumbar, or sacral. The cervical portion of the spine extends from the base of the skull and includes the first seven vertebrae. The intermediate twelve vertebrae make up the thoracic portion of the spine. The lower portion of the spine comprises five lumbar vertebrae. The base of the spine is the sacral bones (including the coccyx). The component bones of the cervical spine are generally smaller than those of the thoracic spine, which are in turn smaller than those of the lumbar region. The sacral region connects laterally to the pelvis. While the sacral region is an integral part of the spine, for the purposes of fusion surgeries and for this disclosure, the word spine shall refer only to the cervical, thoracic, and lumbar regions.

Bone fixation devices are useful in treating and repairing vertebral bone segments damaged due to trauma, degenerative disc diseases, or other injurious causes. Fixation devices immobilize the vertebral segments to prevent further damage and to encourage and ensure proper healing and growth of new bone. These fixation devices often include bracing or instrumentation to stabilize adjacent vertebral bodies and the spine. Properly used, implantable fixation devices allow for minimal patient immobilization and successful post-operative care.

An osteosynthesis plate, or a bone fixation plate, can be used to immobilize adjacent boney elements and particularly vertebra and more particularly cervical vertebra. Bone fixation plates are often a metal or rigid polymeric scaffold or plate extending across a single or multiple vertebral bodies. Bone plates are useful for providing mechanical support to keep vertebral bodies in necessary position and bridge a weakened or repaired area of the spine, often when a disc, vertebral body, or fragment has been removed or repaired. The plate can be fixed to the vertebral bodies with bone screws or other fixation devices.

The spinal column is highly complex in that it includes these more than twenty bones coupled to one another, housing and protecting critical elements of the nervous system. It further acts as an attachment point for innumerable peripheral nerves, circulatory, and alimentary structures in close proximity, particularly along its anterior surface. In spite of these complications, the spine is a highly flexible structure, capable of a high degree of curvature and twist in nearly every direction. The spinal column is the central part of the skeleton and acts as a longitudinal support structures on which muscles, organs and other anatomical structures attach to, for support. In general, the posterior the spinal column has attachments for muscles to allow us to standup and move our neck, torso and lower back. The anterior part of the spinal column has fewer muscle attachments and acts as a path along which our nerves, blood vessels, alimentary tract, and other structures are attached and forms a path for these structures. Many of these structures such as blood vessels, nerves, and alimentary canal have lumens through which substances are transported to throughout the body. These substances, such as nourishment or blood, travel in these lumens along a path adjacent to the anterior spinal column. Any fixation devise attached to the anterior column would benefit substantially from not disrupting the natural flow of substances traveling in the lumen of these structures adjacent to the anterior spinal column.

Traditionally, the treatment of choice for physicians caring for patients utilize bone plates that have a plurality of screw openings spanning the plate, which can range in size to cover a single damaged vertebral body, or two or more vertebral bodies. The plate is usually placed against the particular vertebral bodies and the bone screws are driven into the bone, which secures the plate to the spine and prevents movement between the adjacent vertebral bodies. Plates are generally elongated to span the distance between two, three, or more vertebrae. The bone plates are generally curved transversely, or horizontally relative to the spinal mid-line, to fit the curvature of the cervical spine. Bone plates are commonly constructed with symmetrical shapes including fixation apertures.

Plates may utilize one, two, or more fixation holes at superior edges of the plate and corresponding segments of the vertebral bodies. The superior edge of the plate is relatively flat, perpendicular to the transverse plane of the plate, and/or perpendicular to the sagittal plane of the spine. While this orientation is sufficient for securing the plate to the vertebral bodies, the design interferes with the flow of substances through the lumen of anatomic structures that rest on or engage with the plate. In order to accommodate adequate space for one or more bone fixation anchors, these plates' edges, which run perpendicular to the direction of travel within the lumen, create an obstruction to the flow within the lumen. Existing plates operate similarly to a dam across a river.

In particular, when these cervical plates are affixed to the anterior cervical spine, patients commonly have difficulty swallowing. Sometimes, the swallowing difficulty requires intervention from other specialists, which may include placement of a feeding tube. Anatomically, the esophagus rests near the cervical spine. When a patient swallows, a bolus of substance passes through the esophagus and across the superior edge of the cervical plate. This often causes pain, discomfort, or swallowing difficulty for the patient. It is clear that the use of an anterior cervical plate with a flat superior edge creates a dam-effect restricting movement of substances in the esophagus. This effect is undesirable from the perspective of the patient's quality of life, as well as from the perspective of possibly pushing a patient to undergo multiple other treatments and the symptoms sometimes never resolve.

Patients with an anterior cervical plate often have to adjust their daily life to cope with this issue. Some patients have addressed the issue by turning the head to adjust the esophagus to be non-perpendicular to the superior edge of the anterior cervical plate. Notwithstanding the development of the prior art to date, a need exists for improvements in cervical plates specifically suited for anterior placement to address swallowing difficulty for patients. This need has been addressed by making the plate as thin as possible. Although this design has helped, it has not eliminated the problem. Further, thin plates may structurally fail due to their thinness.

The objective of the present invention is a novel cervical bone plate designed particularly for the anterior side of the cervical spine, which substantially overcomes the problems of the prior art, which creates swallowing difficulty and esophageal damage. By having an anterior cervical plate with a superior edge at an angle to the transverse plane with a rounded or cambered edge, a bolus can traverse the esophagus without abruptly abutting the superior edge of the cervical plate.

Further by providing an anterior cervical plate with a single screw at the superior end, the general cost of manufacturing and complexity of implantation is reduced and surgical time is decreased.

Further by manufacturing such an implant with 3D printing technology a significant cost savings can be obtained.

Further, by improving a patient's post-operative ability to return to a normal lifestyle, the quality of life, and complication rates associated with the surgery is reduced.

These and other objectives will become apparent from the following description of the invention.

SUMMARY OF THE INVENTION

In some embodiments, the present disclosure provides a system for anterior fixation of the spine, the system including: an asymmetric plate, the asymmetric plate having: an exterior surface, an interior surface, a superior edge and an inferior edge connected by perimeter edges, wherein the superior edge is curved between the interior surface and the exterior surface, and a plurality of apertures; and a plurality of bone fixation elements. The interior surface may be concave complementarily to anterior surfaces of cervical vertebrae. The interior surface may be juxtaposed next to the anterior surfaces of cervical vertebrae, the superior edge may extend from a first vertebra to a second vertebra and the inferior edge may extend from the first vertebra to the second vertebra. When the interior surface is juxtaposed next to the anterior surfaces of cervical vertebrae, the superior edge may extend from a first side of the median plane of the spine to a second side of the median plane of the spine and the inferior edge may extend from a first side of the median plane of the spine to a second side of the median plane of the spine. When the interior surface is juxtaposed next to the anterior surfaces of cervical vertebrae, the superior edge may be adjacent a first vertebra on a first side of a median plane of the spine and may extend across the median plane to a second vertebra on a second side of the median plane, and the inferior edge may extend along a second vertebra from the first side of the median plane of the spine to the second side of the median plane of the spine. The plurality of apertures may include a first bone fixation hole and a second bone fixation hole, and wherein when the interior surface is juxtaposed next to the anterior surfaces of cervical vertebrae, the first bone fixation hole may be adjacent to a first vertebra and the second bone fixation hole may be adjacent to a second vertebra. The superior edge may extend across the asymmetric plate generally between the first bone fixation hole and the second bone fixation hole. When the interior surface is juxtaposed next to the anterior surfaces of cervical vertebrae, the first bone fixation hole and the second bone fixation hole may be on diagonally opposing points on the first vertebra and the second vertebral, across the median plane of the spine and across an intervertebral space separating the first vertebra and the second vertebra. The superior edge may cross the median plane of the spine diagonally. The superior edge may include a camber between the first bone fixation hole and the second bone fixation hole. The plurality of bone fixation elements may further include at least two bone screws capable of passing through two of the plurality of apertures into a first vertebra and a second vertebra. The plurality of bone fixation elements may further include at least one anti-backout feature configured to prevent the movement of at least one of the at least two bone screws relative to the asymmetric plate. At least one of the plurality of apertures may be configured to secure the plate to at least one intervertebral implant.

In some embodiments, the present disclosure provides a system for anterior fixation of the spine, the system including: an asymmetric plate having a longitudinal axis extending in a longitudinal direction and a transverse axis extending in a transverse direction, the asymmetric plate having: an exterior surface, an interior surface, a superior edge and an inferior edge connected by perimeter edges, wherein the superior edge is curved between the interior surface and the exterior surface, and a plurality of apertures; and a plurality of bone fixation elements; wherein the asymmetric plate is asymmetric across both the longitudinal axis and the transverse axis; and wherein the asymmetric plate is configured to bridge at least two vertebrae. The interior surface may be concave complementarily to anterior surfaces of cervical vertebrae, and wherein the asymmetric plate may be configured to be affixed to anterior cervical vertebrae such that when affixed the longitudinal axis of the asymmetric plate is aligned with a median plane of the spine; wherein the plurality of apertures may include a first bone fixation hole and a second bone fixation hole, and when the interior surface is juxtaposed next to the anterior surfaces of cervical vertebrae, the first bone fixation hole may be adjacent to a first vertebra and the second bone fixation hole may be adjacent to a second vertebra and the superior edge may extend generally between the first bone fixation hole and the second bone fixation hole. The inferior edge may extend across a second vertebra across the median plane of the spine. The inferior edge may extend across a third vertebra across the median plane of the spine. The superior edge may cross the median plane of the spine diagonally across an intervertebral space; and wherein the superior edge has a camber between the first bone fixation hole and the second bone fixation hole.

In some embodiments, the present disclosure provides a system for anterior fixation of the spine, the system including: an asymmetric plate having a longitudinal axis extending in a longitudinal direction and a transverse axis extending in a transverse direction, the asymmetric plate having: an exterior surface, an interior surface, a superior edge and an inferior edge connected by perimeter edges, wherein the superior edge is curved between the interior surface and the exterior surface; and a plurality of apertures; and a plurality of bone fixation elements; wherein the asymmetric plate is asymmetric across both the longitudinal axis and the transverse axis; and wherein the asymmetric plate is configured to bridge at three vertebrae. When the asymmetric plate is attached to the anterior spine: the plurality of apertures may include a first bone fixation hole configured to be adjacent a first vertebra and a second bone fixation hole configured to be adjacent a second vertebra; the superior edge may cross the median plane of the spine diagonally across an intervertebral space; the inferior edge may extend across a third vertebra across the median plane of the spine; and wherein the superior edge has a camber between the first bone fixation hole and the second bone fixation hole.

BRIEF DESCRIPTION OF THE DRAWINGS

Exemplary embodiments of the invention will become more fully apparent from the following description and appended claims, taken in conjunction with the accompanying drawings. Understanding that these drawings depict only exemplary embodiments and are, therefore, not to be considered limiting of the invention's scope, the exemplary embodiments of the invention will be described with additional specificity and detail through use of the accompanying drawings in which:

DETAILED DESCRIPTION OF THE INVENTION

Exemplary embodiments of the invention will be best understood by reference to the drawings, wherein like parts are designated by like numerals throughout. It will be readily understood that the components of the invention, as generally described and illustrated in the Figures herein, could be arranged and designed in a wide variety of different configurations. Thus, the following more detailed description of the embodiments of the apparatus, as represented in FIGS. 1 through 6, is not intended to limit the scope of the invention, as claimed, but is merely representative exemplary of exemplary embodiments of the invention.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The term "adjacent" refers to items that are physically near or next to one another and may or may not be in physical contact. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Standard anatomical reference planes and spinal terminology are used in this specification with their customary meanings.

The details of one or more embodiments of the invention are set forth in the accompanying description below. Although any materials and methods similar or equivalent to those described herein can be used in the practice or testing of the present invention, the preferred materials and methods are now described. Other features, objects and advantages of the invention will be apparent from the description. In the description, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present description will control.

Figure 1:
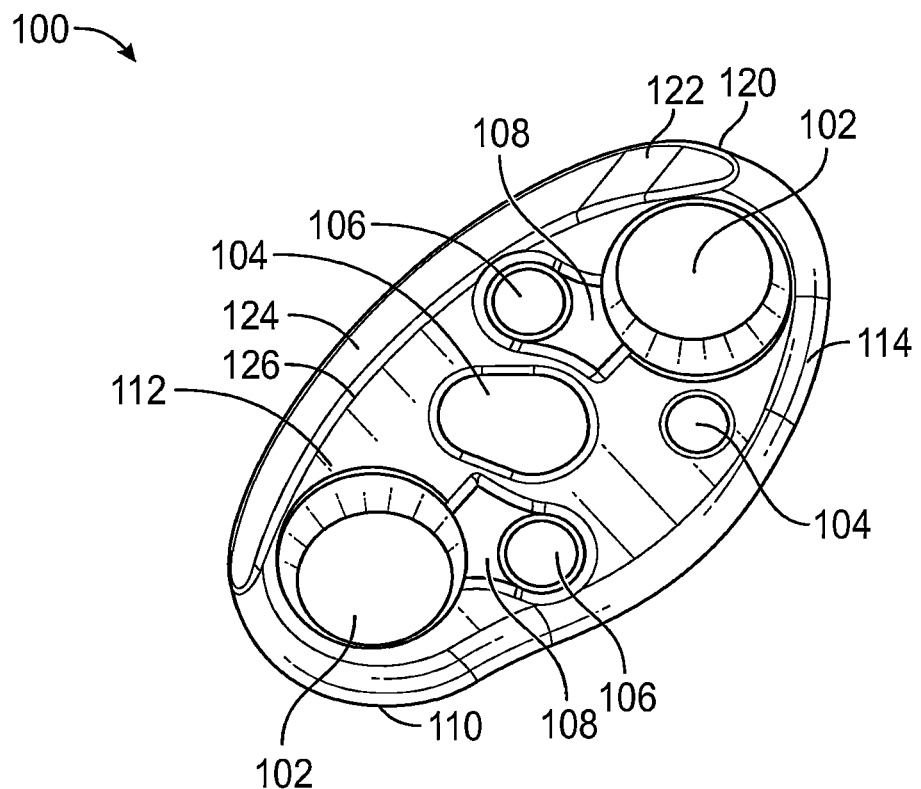
FIG. 1 shows an anterior view of a cervical plate.
Figure 2:
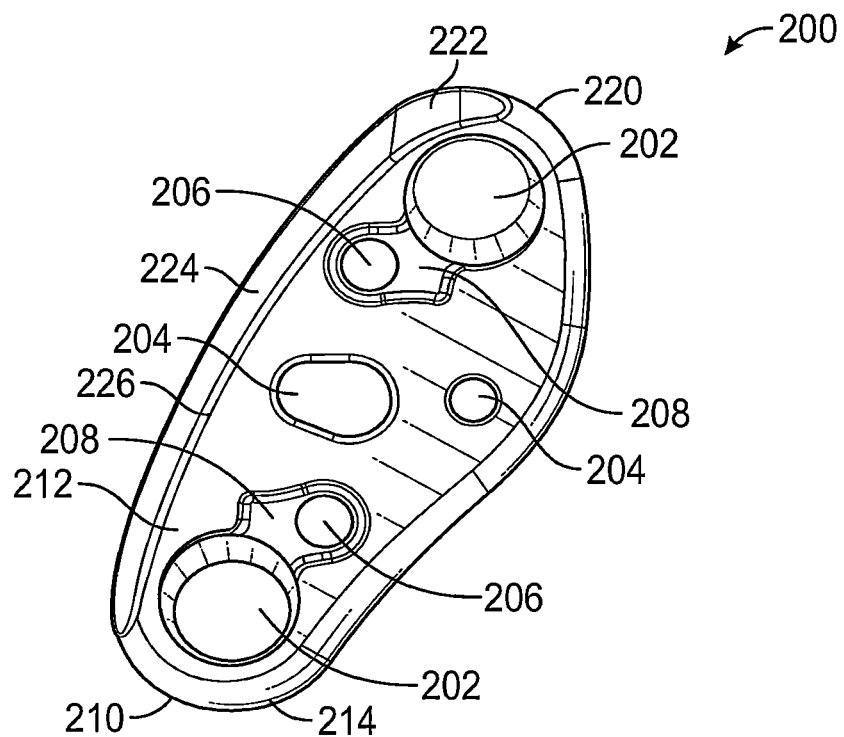
FIG. 2 shows an anterior view of a cervical plate.
Figure 3:
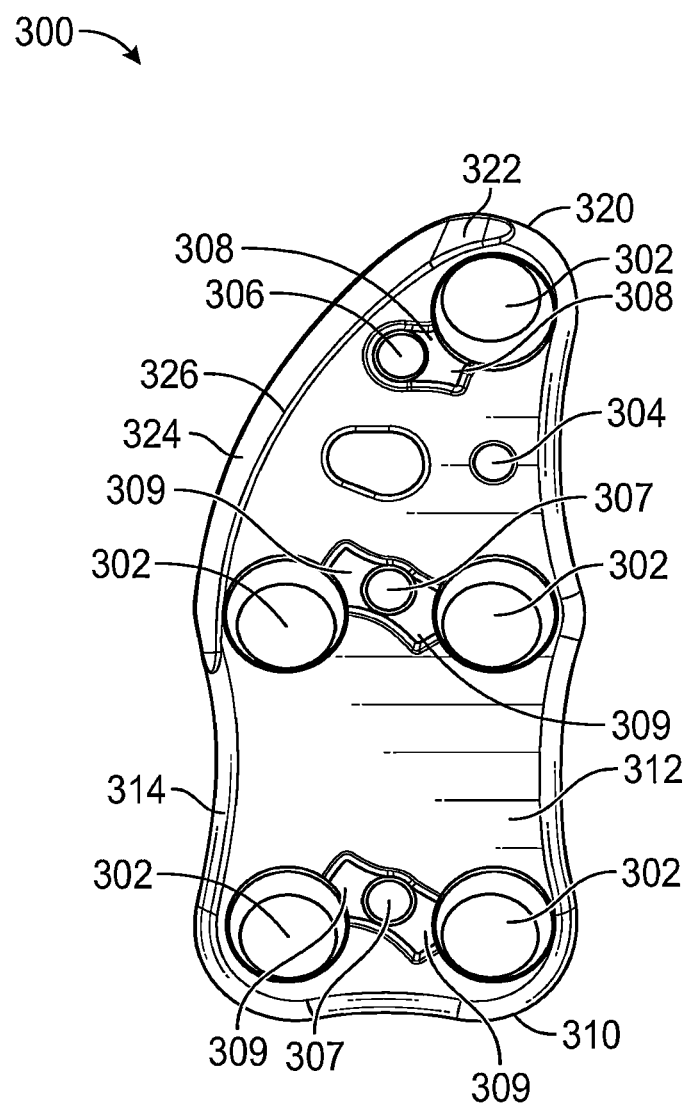
FIG. 3 shows an anterior view of a cervical plate for three vertebrae.

FIGS. 1-3 illustrate by way of example only, a plate that may be used to stabilize or fuse the vertebral bodies in the cervical, or other region of the spine. The plates in FIGS. 1-3 may be preferably implanted on the anterior side of the cervical spine. FIGS. 1 and 2 depict a single level bone fixation plate that is configured to span across two vertebrae and secures into adjacent vertebral bodies by fixation devices, such as screws.

FIG. 1 shows an anterior cervical plate 100 suitable for securing to two adjacent vertebral bodies, on the anterior side of the cervical spine. The plate 100 has an anterior face 112 opposite a posterior face (not shown). The posterior face is positioned against a patient's vertebral bodies to be immobilized. The anterior face 112 is positioned toward the patient's soft tissue and esophagus, when implanted. The plate 100 has an inferior edge 110 generally opposite the superior edge 120.

The superior edge 120 and the inferior edge 110 are interconnected by generally rounded edges 114 about the perimeter of the plate 100. The perimeter of the plate 100 and the rounded edges 114 create a non-regular shape, such as a tear drop or what may be considered a portion of a herringbone pattern. The plate 100 is asymmetric across the spinal midline or medial plane of the body.

The plate 100 does not have any straight edges or converging surfaces that form an acute angle. Most notably, plate 100 has a cambered slope side 124 that is on a more superior side of the plate 100 and generally cross the spinal midline. The cambered slope side 124 may further include a curved portion 122 that is on or adjacent to the superior edge 120 of the plate 100. The curved portion 122 and the cambered slope side 124 are oriented so that the soft tissue of a patient's esophagus or other vessel engages the curved portion 122 or the cambered slope side 124 first, as a bolus passes down the esophagus. Contrasted with anterior cervical plates in the prior art, the curved portion 122 and the cambered slope side 124 provide a gentle interaction with the esophagus, absent any acute angles or square edges, which are more likely to catch on the esophagus as the bolus passes or slow the passage of the bolus. The impediment of the esophagus causes pain and discomfort to the patient.

The curved portion 122 acts as a leading or guiding edge transitioning into the cambered slope side 124. The cambered slope side 124 is configured to allow a bolus passing through the esophagus to pass the plate 100 with limited engagement and reduced impediment. The configuration of the curved portion 122 and the cambered slope side 124 are reflected in the asymmetric shape in such a way that the bolus passing through the esophagus first traverses a directional edge of the plate 100. Because the curved portion 122 is offset, or to one side of the sagittal plane, the bolus is encouraged to pass along only one side of the plate 100, which should be toward the cambered slope side 124.

FIG. 1 depicts two fastener through-holes 102 spaced out along the plate 100 for driving fasteners 350 into and stabilizing two vertebral bodies. Each through-hole 120 is adapted for receiving a fastener 350 to be driven into a single vertebral body. Each through-hole 120 diverges slightly offset laterally from a longitudinal axis (in the medial plane) of the plate 100. Each fastener through-hole may have a concave perimeter to match a convex surface of the underside of a fastener head so that the fastener 350 is generally flush with, or recessed with respect to, the anterior face 112 of the plate 100.

In order to prevent the backing out of the fastener 350, adjacent to each through-hole is a locking element opening 106 adapted to receive locking elements 351. Locking elements 351 may include a set screw having a threaded shaft and a single wing 352. The locking element 351 may be fixed within the locking element opening, so that the single wing 352 rests on the wing plateau 108. The wing plateau is a recessed plane or plateau just beneath the plane of the anterior face 112. The single wing 352 is configured to transition from primarily on the wing plateau 108 to covering the fastener. By covering the fastener, the single wing acts as an anti-backout mechanism to prevent the fastener 350 from backing out of the though hole 120 and the vertebral body. The fastener may be rotatable from a first position over the wing plateau 352 to over the fastener 350 via torquing a head of the fastener 350 with a driver. The plate 100 may also have at least one aperture 104, which provides an opportunity for bone ingrowth or alternative fixation of the plate 100 to the vertebral body. The aperture 104 also improves manufacturing as it reduces weight of the plate 100.

FIG. 2 shows an anterior cervical plate 200 suitable for securing to two adjacent vertebral bodies, on the anterior side of the cervical spine. The plate 200 has an anterior face 212 opposite a posterior face (not shown). The posterior face is positioned against a patient's vertebral bodies to be immobilized. The anterior face 212 is positioned toward the patient's soft tissue and esophagus, when implanted. The plate 200 has an inferior edge 210 generally opposite the superior edge 220. The superior edge 220 and the inferior edge 210 are interconnected by generally rounded edges 214 about the perimeter of the plate 200. The perimeter of the plate 200 and the rounded edges 214 create a non-regular shape, such as a tear drop or what may be considered a portion of a herringbone pattern. The plate 200 is asymmetric across the sagittal plane of the body. Plate 200 is designed to be stacked along the spine and nest next to a preceding plate 200.

The plate 200 does not have any straight edges or converging surfaces that form an acute angle. Most notably, plate 200 has a cambered slope side 224 that is on a more superior side of the plate 200. The cambered slope side 224 may further include a curved portion 222 that is on or adjacent to the superior edge 220 of the plate 200. The curved portion 222 and the cambered slope side 224 are oriented so that the soft tissue of a patient's esophagus engages the curved portion 222 first, as a bolus passes down the esophagus. Contrasted with anterior cervical plates in the prior art, the curved portion 222 and the cambered slope side 224 provide a gentle interaction with the esophagus, absent any acute angles or square edges, which are more likely to catch on the esophagus as the bolus passes or slow the passage of the bolus. The impediment of the esophagus causes pain and discomfort to the patient.

The curved portion 222 acts as a leading or guiding edge transitioning into the cambered slope side 224. The cambered slope side 224 is configured to allow a bolus passing through the esophagus to pass the plate 200 with limited engagement and reduced impediment. The configuration of the curved portion 222 and the cambered slope side 224 are reflected in the asymmetric shape in such a way that the bolus passing through the esophagus first traverses a directional edge (not perpendicular to the spinal midline) of the plate 200. Because the curved portion 222 is offset, or to one side of the medial plane, the bolus is encouraged to pass gently along only one side of the plate 200, which should be toward the cambered slope side 224.

FIG. 2 depicts two fastener through-holes 202 spaced out along the plate 200 for driving fasteners 350 into and stabilizing two vertebral bodies. Each through-hole 220 is adapted for receiving a fastener 350 to be driven into a single vertebral body. Each through-hole 220 diverges slightly offset laterally from a longitudinal axis (in a medial plane) of the plate 200. Each fastener through-hole may have a concave perimeter to match a convex surface of the underside of a fastener head so that the fastener 350 is generally flush with, or recessed with respect to, the anterior face 212 of the plate 200.

In order to prevent the backing out of the fastener 350, adjacent to each through-hole is a locking element opening 206 adapted to receive locking elements 351. Locking elements 351 may include a set screw having a threaded shaft and a single wing 352. The locking element 351 may be fixed within the locking element opening, so that the single wing 352 rests on the wing plateau 208. The wing plateau is a recessed plane or plateau just beneath the plane of the anterior face 212. The single wing 352 is configured to transition from primarily on the wing plateau 208 to covering the fastener. By covering the fastener, the single wing acts as an anti-backout mechanism to prevent the fastener 350 from backing out of the though hole 220 and the vertebral body. The fastener may be rotatable from a first position over the wing plateau 352 to over the fastener 350 via torquing a head of the fastener 350 with a driver. The plate 200 may also have at least one aperture 204, which provides an opportunity for bone ingrowth or alternative fixation of the plate 200 to the vertebral body. The aperture 204 also improves manufacturing as it reduces weight of the plate 200.

FIG. 3 shows an anterior cervical plate 300 suitable for securing to three adjacent vertebral bodies, on the anterior side of the cervical spine. The plate 300 has an anterior face 312 opposite a posterior face (not shown). The posterior face is positioned against a patient's vertebral bodies to be immobilized. The anterior face 312 is positioned toward the patient's soft tissue and esophagus, when implanted. The plate 300 has an inferior edge 310 generally opposite the superior edge 320. The superior edge 320 and the inferior edge 310 are interconnected by generally rounded edges 314 about the perimeter of the plate 300. The perimeter of the plate 300 and the rounded edges 314 create a non-regular shape, with a single apex at the superior side and a flat inferior side, or a tear drop or what may be considered a portion of a herringbone pattern. The plate 300 is asymmetric across the sagittal plane of the body.

The plate 300 does not have any straight edges or converging surfaces that form an acute angle. Most notably, plate 300 has a cambered slope side 324 that is on a more superior side of the plate 300. The cambered slope side 324 may further include a curved portion 322 that is on or adjacent to the superior edge 320 of the plate 300. The curved portion 322 is oriented so that the soft tissue of a patient's esophagus engages the curved portion 322 and the cambered slope side 324 first, as a bolus passes down the esophagus. Contrasted with anterior cervical plates in the prior art, the curved portion 322 and cambered slope side 324 provide a gentle interaction with the esophagus, absent any acute angles or square edges, which are more likely to catch on the esophagus as the bolus passes or slow the passage of the bolus. The impediment of the esophagus causes pain and discomfort to the patient.

The curved portion 322 acts as a leading or guiding edge transitioning into the cambered slope side 324. The cambered slope side 324 is configured to allow a bolus passing through the esophagus to pass the plate 300 with limited engagement and reduced impediment. The configuration of the curved portion 322 and the cambered slope side 324 are reflected in the asymmetric shape in such a way that the bolus passing through the esophagus first traverses a directional edge of the plate 300. Because the curved portion 322 is offset, or to one side of the medial plane, the bolus is encouraged to pass along only one side of the plate 300, which should be toward the cambered slope side 324.

FIG. 3 depicts five fastener through-holes 302 spaced out along the plate 300 for driving fasteners 350 into and stabilizing two vertebral bodies. Each through-hole 302 is adapted for receiving a fastener 350 to be driven into a single vertebral body. Each single through-hole 320 diverges slightly offset laterally from a longitudinal axis (in a sagittal plane) of the plate 300. Each fastener through-hole may have a concave perimeter to match a convex surface of the underside of a fastener head so that the fastener 350 is generally flush with, or recessed with respect to, the anterior face 312 of the plate 300. In an embodiment, such as shown in FIG. 3, that spans several vertebral bodies, the uppermost fastener through hole 302 aligns with lower through holes 302. This alignment may be generally parallel and offset from the spinal midline. FIG. 3 depicts the alignment on the right side of the plate 300 with the cambered slope side 324 on the left. It is within the scope of the invention to have a plate 300 with an opposite or mirrored orientation. Further, the alignment of superior and inferior through holes 302 may occur in plates not shown in the Figures. For example, a plate that spans two vertebral bodies would have two strata of through holes. To connect the plate to the superior vertebral body, the plate would have a single through hole offset to a side of the spinal midline. Across the spinal midline from the single through hole would be the cambered slope. Attaching the same plate to the inferior vertebral body would be a stratum of two through holes, flanking the spinal midline. One of the lower/inferior through holes would align with the single upper through hole on the same side of the spinal midline. It is also contemplated that when multiple plates, such as plates 100 and 200, are used to span several vertebral bodies, the upper through hole of the superior plate may align with the upper through hole of the inferior plate, and so on.

In order to prevent the backing out of the fastener 350, adjacent to each through-hole is a locking element opening 306 adapted to receive locking elements 351. Locking elements 351 may include a set screw having a threaded shaft and a single wing 352 or a double wing 354. The locking element 351 may be fixed within the locking element opening, so that the single wing 352 rests on the wing plateau 308 or the double wing 354 rests on a double wing plateau 309. The wing plateau is a recessed plane or plateau just beneath the plane of the anterior face 312. The single wing 352 and double wing 354 are configured to transition from primarily on the wing plateau 308 or double wing plateau 309 to covering the fastener 350. By covering the fastener 350, the single wing 352 and double wing 354 acts as anti-backout mechanisms to prevent the fastener 350 from backing out of the though hole 320 and the vertebral body. The fastener may be rotatable from a first position over the wing plateau 352 or double wing plateau 354 to over the fastener 350 via torquing a head of the fastener 350 with a driver. The plate 300 may also have at least one aperture 304, which provides an opportunity for bone ingrowth or alternative fixation of the plate 300 to the vertebral body. The aperture 304 also improves manufacturing as it reduces weight of the plate 300.

Figure 4:
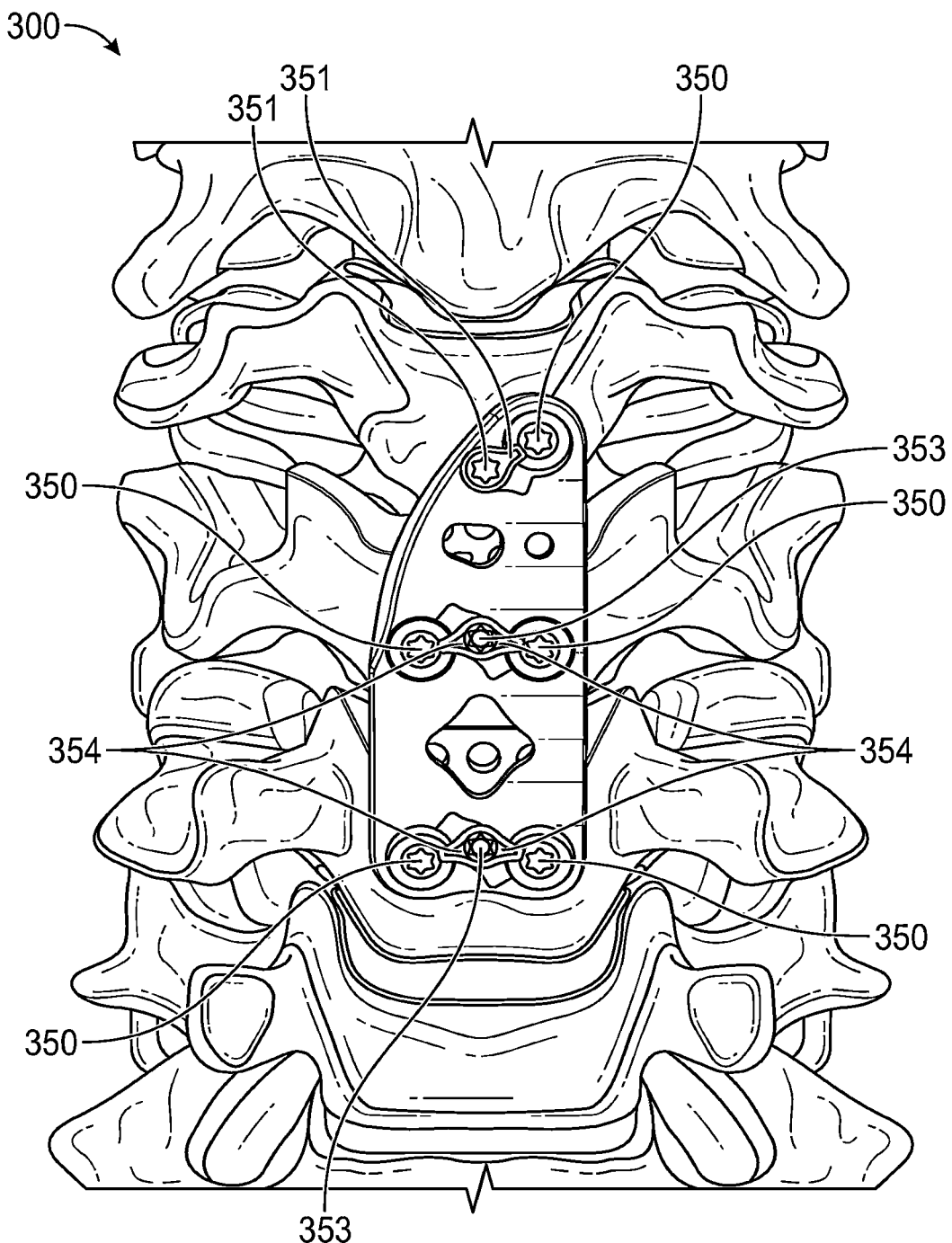
FIG. 4 shows an anterior view of a cervical plate affixed to vertebrae.
Figure 5:
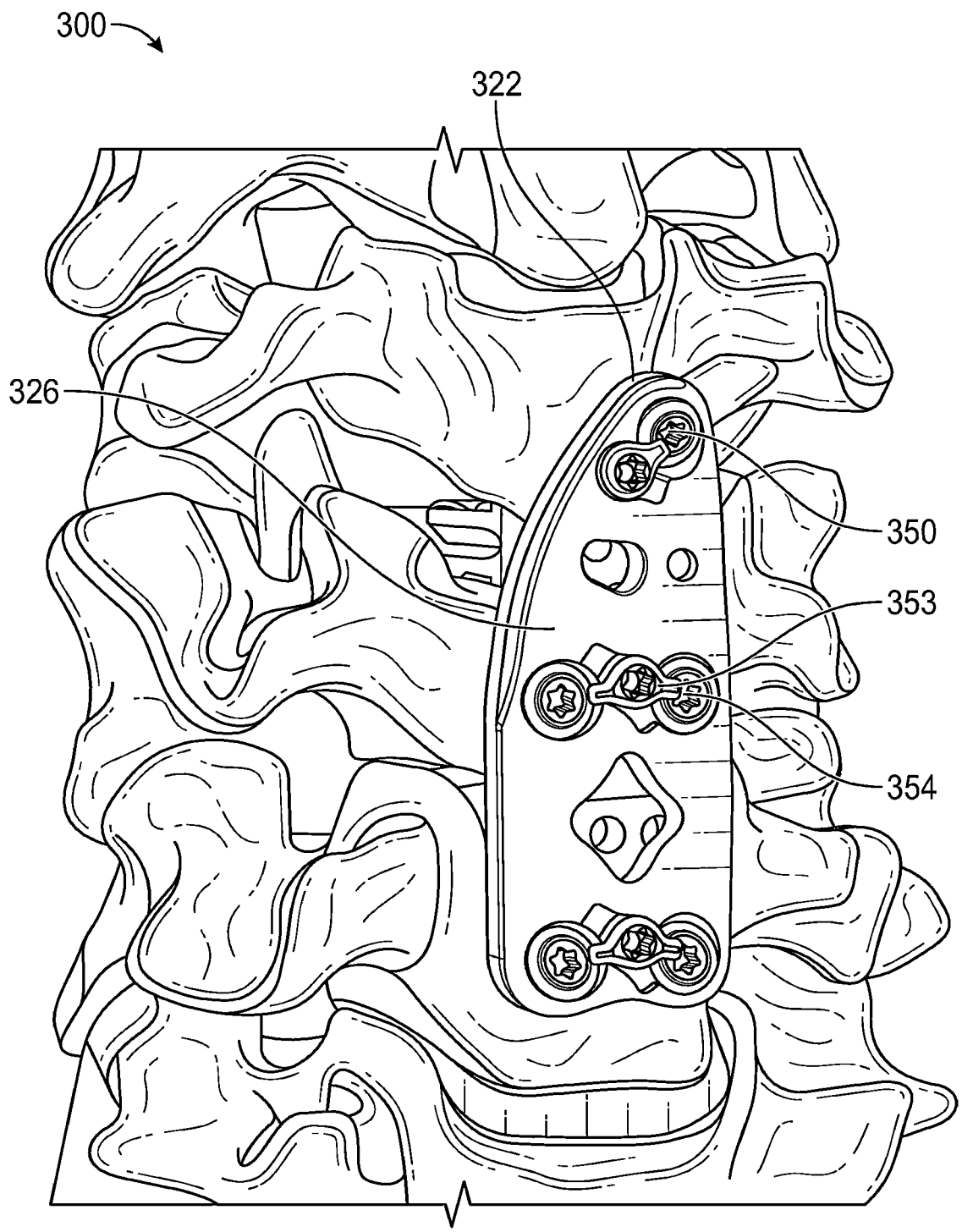
FIG. 5 shows an anterior perspective of the plate in FIG. 4.
Figure 6:
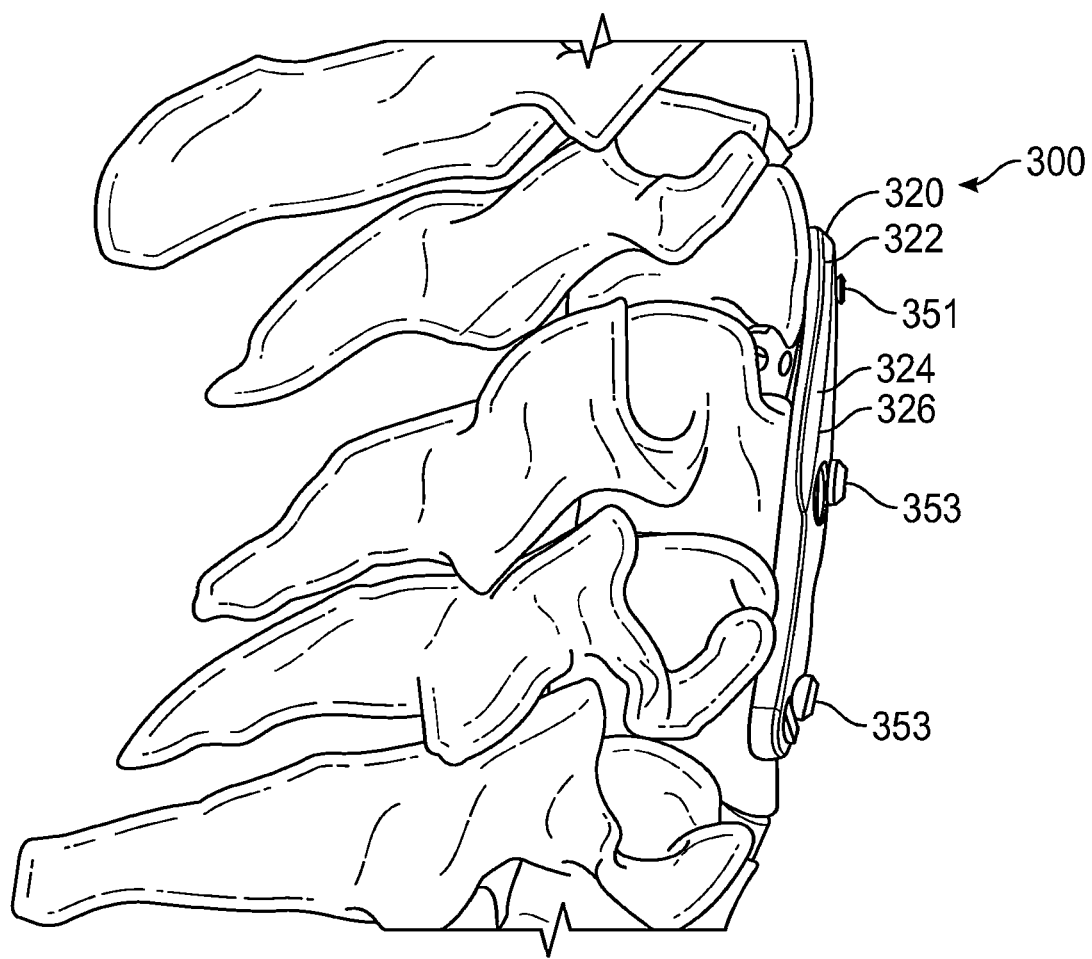
FIG. 6 shows a side perspective of the cervical plate in FIG. 4.

FIGS. 4-6 depict the plate 300 as it is secured to vertebral bodies. FIG. 4 is an anterior view of the cervical spine with a plate 300 that spans three vertebral bodies. The most superior portion of the plate 300 has a single fixation bone screw 350. The more inferior portions of the plate have dual fixation openings 302 for multiple bone screws 350. Plate 300 has multiple apertures 304, which allow for ingrowth as well as weight and cost savings in manufacturing.

FIG. 5 is a view of plate 300 secured to vertebral bodies slightly angled to the cervical spine. FIG. 6 shows the plate 300 at a side angle and shows the low profile of the plate and the angle of the curved portion 322 and how the cambered slope side 324 extends from the curved portion 322, which deflects the bolus traversing the esophagus.

Figure 7:
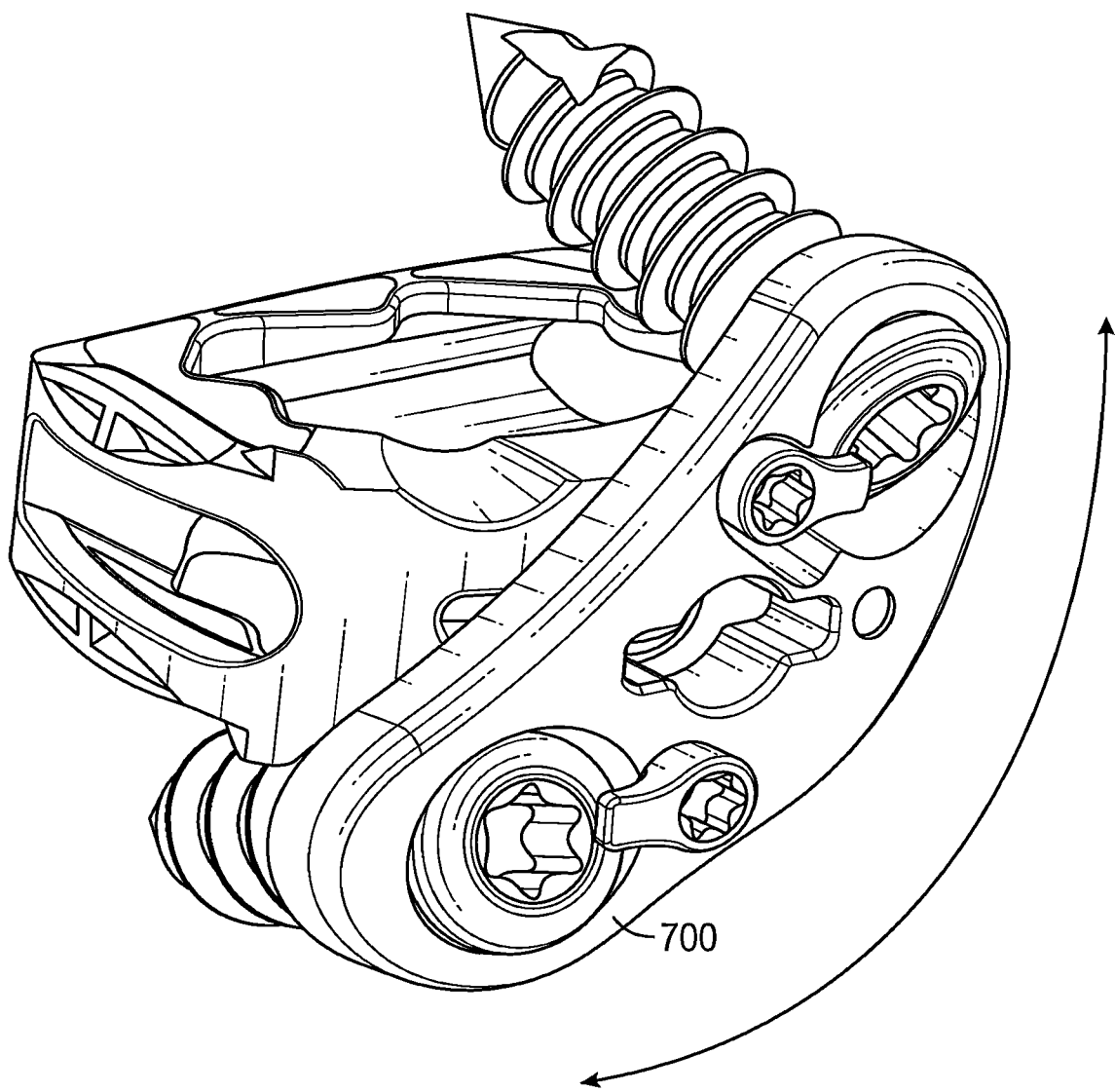
FIG. 7 shows a cervical plate attached to an implant.
Figure 8:
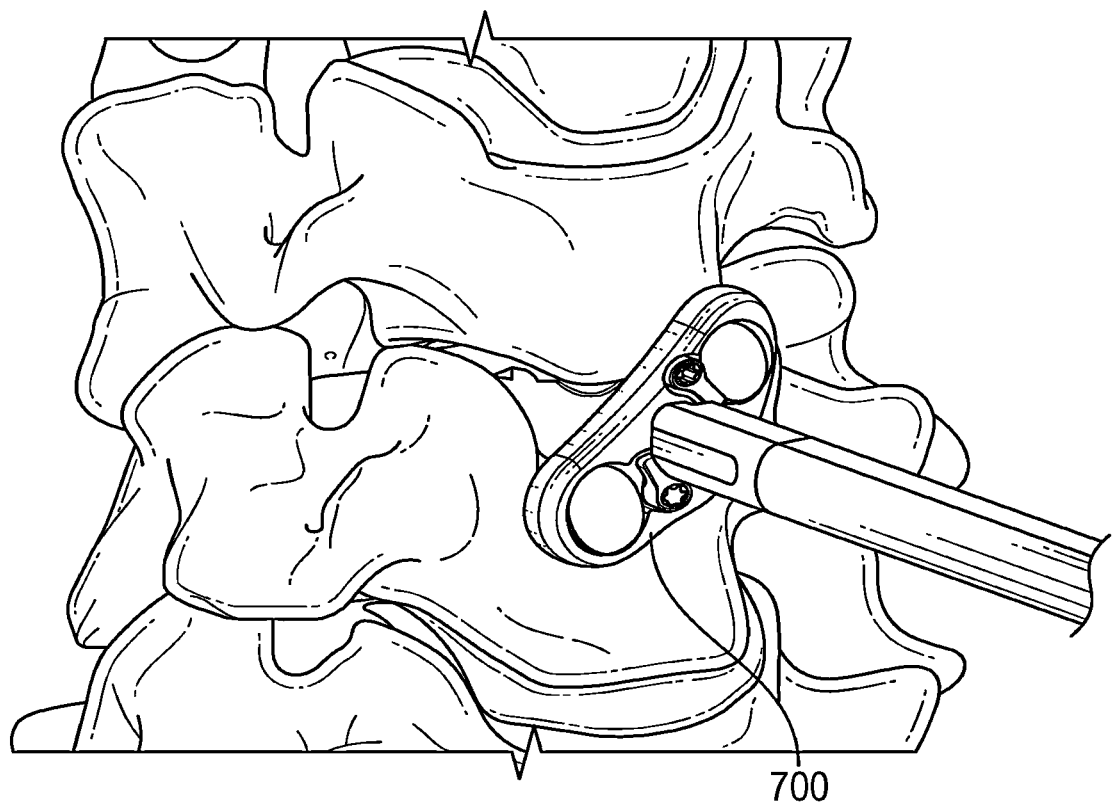
FIG. 8 shows the cervical plate of FIG. 7 affixed to an implant and vertebrae.

FIGS. 7-8 show an embodiment of plate 700, which is shown connected to an implant and positioned between two vertebral bodies in the spine, as in FIG. 8. Plate 700 has a first upper through-hole fixed to the upper vertebral body and a second lower through-hole fixed to the lower vertebral body. The plate 700 spans a single vertebral space between two adjacent vertebral bodies. The plate 700 shows a specific curvature from the lower end up and around the spinal column to the upper end. This curvature mimics a "handedness" that allows the plate to be positioned next to the spine in a general orientation. The orientation of the plate 700 adjacent the spine allows the plate to be asymmetric relative to the spinal midline. The plate 700 may be fixed to an implant inserted between two adjacent vertebral bodies, in addition to fixation to the adjacent vertebral bodies. As shown in FIG. 8, the asymmetry is the upper through-hole being to the right of the spinal midline, or medial plane. The lower through-hole is to the left of the spinal midline or medial plane. The edge of the plate that rests in line with the medial plane may have a more cambered slope to prevent the stoppage of anything traversing the esophagus or other vessel.

All of the plates 100, 200, 300, and 700 may have asymmetry relative to the spinal midline or medial plane. All of the plates 100, 200, 300, and 700 may have a "handedness" as the plates rest against the spinal column, which allow for a specific orientation of the plate on the spine. The asymmetry of any of the contemplated plates may favor the right or left side of the medial plane. While the plates in the FIGS show a superior edge rising to the right of the medial plane, the plates may also have a superior edge rising to the left. It is also contemplated that a series of plates may be attached to several adjacent vertebral bodies. For example, the plates 100 200 700 maybe stacked in a herringbone-like pattern along the spine.

Plates 100 200 300 700 are configured for implantation across two or more adjacent vertebral bodies. In this example, the height extends along a cephalad-caudal direction, the width extends along a right-left direction, and the length extends along an anterior-posterior direction. The anterior cervical plates 100 200 300 700 may be made of any suitable biocompatible material. Various biocompatible materials contemplated include, but are not limited to, poly-ether-ether-ketone (PEEK), other polymers including bioresorbable polymers, ceramics, composites, bone or bone substitute materials, and biocompatible metals including stainless steel, titanium, or tantalum and their alloys. The anterior cervical plates 100 200 300 may also include multiple and combinations of the materials. The anterior cervical plates 100 200 300 may be manufactured by known methods such as machining, molding, forming, or 3D printing. The cage 100 may be provided in any number of shapes or sizes depending on the specific surgical procedure, need, or patient anatomy. The anterior cervical plates 100 200 300 may contain separate radiographic markers of any size of shape suitable to facilitate effective and accurate visualization of implant placement, necessary depending on the base material of the implant.

EQUIVALENTS AND SCOPE

Those skilled in the art will recognize or be able to ascertain using no more than routine experimentation, many equivalents to the specific embodiments in accordance with the invention described herein. The scope of the present invention is not intended to be limited to the above Description, but rather is as set forth in the appended claims.

Any methods disclosed herein comprise one or more steps or actions for performing the described method. The method steps and/or actions may be interchanged with one another and applicable to all embodiments of the intervertebral body implants described herein. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the invention.

While specific embodiments and applications of the present invention have been illustrated and described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any antibiotic, therapeutic or active ingredient; any method of production; any method of use; etc.) can be excluded from any one or more claims, for any reason, whether or not related to the existence of prior art.

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

The invention claimed is:

1. A system for anterior fixation of a spine, the system comprising:

a multi-level vertebral plate comprising:
an upper portion and a lower portion,
a longitudinal axis extending along a length of the vertebral plate,
a concave superior edge and a convex inferior edge connected by a plurality of curved perimeter edges, the superior, inferior, and perimeter edges together defining a profile of the vertebral plate which is entirely curvilinear,
an exterior surface,
an interior surface configured such that the longitudinal axis is configured to align with a median plane of the spine,
wherein the superior edge defines an upper-most extent of the upper portion and is curved continuously between a first perimeter edge and an opposing second perimeter edge of the plurality of curved perimeter edges,
wherein the superior edge comprises a cambered slope and is curved between the interior surface and the exterior surface, and
a plurality of fastener apertures, the plurality of fastener apertures comprising in the upper portion a single fastener aperture and a first set of fastener apertures directly adjacent to the single fastener aperture, and in the lower portion a second set of fastener apertures;
wherein the vertebral plate is configured such that when the longitudinal axis is aligned with the median plane, only the single fastener aperture in the upper portion is juxtaposed adjacent to a first vertebra of the spine and is on a first side of the median plane, the first set of fastener apertures is juxtaposed adjacent to a second vertebra of the spine, and the second set of fastener apertures is juxtaposed adjacent to a third vertebra of the spine with one aperture of the second set of fastener apertures on a second side of the median plane, and wherein the single fastener aperture is coaxial with at least one of the first set of fastener apertures and at least one of the second set of fastener apertures.

2. The system of claim 1, wherein the first side of the median plane is on the right side, anteriorly, of the median plane and the second side of the median plane is on the left side, anteriorly, of the median plane.

3. The system of claim 2, wherein the superior edge extends across the upper portion generally between the single fastener aperture and the first set of fastener apertures.

4. The system of claim 3, wherein the cambered slope extends generally between the single fastener aperture and the first set of fastener apertures on the second side of the median plane.

5. The system of claim 1, further comprising a plurality of bone fixation elements each configured to be received in one of the plurality of fastener apertures and into the first vertebra and the second vertebra.

6. The system of claim 5, further comprising at least one locking element configured to prevent movement of at least one of the plurality of bone fixation elements relative to the vertebral plate.

7. The system of claim 5, further comprising an implant aperture configured to secure the vertebral plate to at least one intervertebral implant.

8. The system of claim 1, wherein the multi-level vertebral plate further comprises:
at least one locking element and at least one corresponding locking element opening configured to securely receive the at least one locking element.

9. The system of claim 8, wherein the at least one locking element comprises a fastener having a wing and the locking element opening comprises a plateau, the plateau abuts the single fastener aperture, and
wherein the system is configured so that when the fastener is securely received into the corresponding locking element opening, the wing extends across the plateau and over the single fastener aperture.

10. The system of claim 8, wherein the at least one locking element comprises a fastener having a first wing and a second wing, and the locking element opening comprises a first plateau and a second plateau, wherein the first plateau abuts one of the apertures in the first set of fastener apertures and the second plateau abuts the other of the apertures in the first set of fastener apertures, and
wherein the system is configured so that when the fastener is securely received into the corresponding locking element opening, the first wing extends across the first plateau and over one of the fastener apertures and the second wing extends across the second plateau and over the other of the fastener apertures.

11. A system for anterior fixation of a spine, the system comprising:
a multi-level vertebral plate comprising:
an asymmetric upper portion and a lower portion,
a longitudinal axis extending along a length of the vertebral plate,
a concave superior edge and a convex inferior edge connected by a plurality of curved perimeter edges, the superior, inferior, and perimeter edges together defining a profile of the vertebral plate which is entirely curvilinear,
an exterior surface,
an interior surface configured such that the longitudinal axis is configured to align with a median plane of the spine,
wherein the superior edge defines an upper-most extent of the upper portion and is curved continuously between a first perimeter edge and an opposing second perimeter edge of the plurality of curved perimeter edges,
wherein the superior edge comprises a cambered slope and is curved between the interior surface and the exterior surface,
at least one aperture in the upper portion capable of bone ingrowth,
a plurality of fastener apertures, the plurality of fastener apertures being countersunk relative to the exterior surface of the vertebral plate, and comprising in the upper portion a single fastener aperture, and in the lower portion a first set of fastener apertures directly adjacent to the single fastener aperture;
wherein the vertebral plate is configured such that when the longitudinal axis is aligned with the median plane, only the single fastener aperture in the upper portion is juxtaposed adjacent to a first vertebra of the spine and is on a first side of the median plane, the first set of fastener apertures is juxtaposed adjacent to a second vertebra of the spine, with one aperture of the first set of fastener apertures positioned coaxial with the single fastener aperture and the other aperture of the first set on a second side of the median plane.

12. The system of claim 11, wherein the superior edge extends across the upper portion generally between the single fastener aperture to the first set of fastener apertures of the lower portion.

13. The system of claim 11, wherein the multi-level vertebral plate further comprises:
at least one locking element and at least one corresponding locking element opening configured to securely receive the at least one locking element.

14. The system of claim 13, wherein the at least one locking element comprises a fastener having a wing and the locking element opening comprises a plateau, the plateau abuts the single fastener aperture, and
wherein the system is configured so that when the fastener is securely received into the corresponding locking element opening, the wing extends across the plateau and over the single fastener aperture.

15. The system of claim 13, wherein the at least one locking element comprises a fastener having a first wing and a second wing, and the locking element opening comprises a first plateau and a second plateau, wherein the first plateau abuts one of the apertures in the first set of fastener apertures and the second plateau abuts the other of the apertures in the first set of fastener apertures, and
wherein the system is configured so that when the fastener is securely received into the corresponding locking element opening, the first wing extends across the first plateau and over one of the fastener apertures and the second wing extends across the second plateau and over the other of the fastener apertures.

16. A system for anterior fixation of a spine, the system comprising:
a multi-level vertebral plate comprising:
an asymmetric upper portion and a lower portion,
a longitudinal axis extending along a length of the vertebral plate,
a concave superior edge and a convex inferior edge connected by a plurality of curved perimeter edges, the superior, inferior, and perimeter edges together defining a profile of the vertebral plate which is entirely curvilinear,
an exterior surface,
an interior surface configured such that the longitudinal axis is configured to align with a median plane of the spine,
wherein the superior edge defines an upper-most extent of the upper portion and is curved continuously between a first perimeter edge and an opposing second perimeter edge of the plurality of curved perimeter edges,
wherein the superior edge comprises a cambered slope and is curved between the interior surface and the exterior surface, and
a plurality of fastener apertures, the plurality of fastener apertures comprising in the upper portion a single fastener aperture and a first set of fastener apertures directly adjacent to the single fastener aperture, and in the lower portion a second set of fastener apertures directly adjacent to the first set of fastener apertures;
wherein the vertebral plate is configured such that when the longitudinal axis is aligned with the median plane, only the single fastener aperture in the upper portion is juxtaposed adjacent to a first vertebra of the spine and is on a first side of the median plane, the first set of fastener apertures is juxtaposed adjacent to a second vertebra of the spine, and the second set of fastener apertures is juxtaposed adjacent to a third vertebra of the spine, wherein one aperture of the second set is coaxial with one aperture of the first set and with the single fastener aperture, and wherein the other aperture of the second set of fastener apertures is on a second side of the median plane.

17. The system of claim 16, further comprising a plurality of bone fixation elements each configured to be received in one of the two of the plurality of fastener apertures and into the first vertebra and the second vertebra.

18. The system of claim 16, wherein the multi-level vertebral plate further comprises:
at least one locking element and at least one corresponding locking element opening configured to securely receive the at least one locking element.

19. The system of claim 18, wherein the at least one locking element comprises a fastener having a wing and the locking element opening comprises a plateau, the plateau abuts the single fastener aperture, and
wherein the system is configured so that when the fastener is securely received into the corresponding locking element opening, the wing extends across the plateau and over the single fastener aperture.

20. The system of claim 18, wherein the at least one locking element comprises a fastener having a first wing and a second wing, and the locking element opening comprises a first plateau and a second plateau, wherein the first plateau abuts one of the apertures in the first set of fastener apertures and the second plateau abuts the other of the apertures in the first set of fastener apertures, and
wherein the system is configured so that when the fastener is securely received into the corresponding locking element opening, the first wing extends across the first plateau and over one of the fastener apertures and the second wing extends across the second plateau and over the other of the fastener apertures.

\* \* \* \* \*